US012708258B2

(12) United States Patent
Leahy et al.

(10) Patent No.: US 12,708,258 B2
(45) Date of Patent: Aug. 18, 2026

(54) LASER SPECKLE REDUCTION IN OPHTHALMIC IMAGES, USING CURRENT PULSE-SHAPING

(71) Applicant: Carl Zeiss Meditec, Inc., Dublin, CA (US)

(72) Inventors: Conor Leahy, Dublin, CA (US); An-Dien Nguyen, Dublin, CA (US); Robert Sprowl, Dublin, CA (US); Jochen Straub, Dublin, CA (US); John Walker, Dublin, CA (US)

(73) Assignee: CARL ZEISS MEDITEC, INC., Dublin, CA (US)

(*) Notice: Subject to any disclaimer, the term of this patent is extended or adjusted under 35 U.S.C. 154(b) by 201 days.

(21) Appl. No.: 18/371,063

(22) Filed: Sep. 21, 2023

(65) Prior Publication Data

US 2024/0108212 A1 Apr. 4, 2024

Related U.S. Application Data

(60) Provisional application No. 63/411,235, filed on Sep. 29, 2022.

(51) Int. Cl.
*A61B 3/00* (2006.01)
*A61B 3/12* (2006.01)

(52) U.S. Cl.
CPC .......... *A61B 3/0008* (2013.01); *A61B 3/0025* (2013.01); *A61B 3/12* (2013.01)

(58) Field of Classification Search
CPC ....... A61B 3/0008; A61B 3/0025; A61B 3/12; A61B 3/14
USPC .......... 351/200
See application file for complete search history.

(56) References Cited

U.S. PATENT DOCUMENTS

2007/0291277 A1* 12/2007 Everett .............. G01B 9/02077 356/497
2009/0025588 A1* 1/2009 Park .............. B82Y 10/00 101/287
2011/0176110 A1* 7/2011 Bublizt .............. G02B 27/0093 351/210
2013/0240709 A1* 9/2013 Ueno .............. H10F 39/8023 257/432
2022/0133212 A1* 5/2022 Krueger .............. A61B 3/0041 600/301
2022/0248952 A1* 8/2022 Laforest .............. A61B 3/12
2023/0210442 A1* 7/2023 Krueger .............. A61B 5/6803 600/301

* cited by examiner

*Primary Examiner* — Mohammed A Hasan
(74) *Attorney, Agent, or Firm* — SNELL & WILMER L.L.P.

(57) ABSTRACT

The eye imaging system for producing images with reduced speckle artifacts may comprise a laser diode for providing a beam of radiation to the eye; a detector for collecting light returning from the eye and generating output signals in response thereto, the detector having a sensor integration time; a driver circuit for applying a modulated drive signal to the laser diode, the modulated drive signal inducing a spectral broadening of the beam of radiation during the sensor integration time. The laser diode may be a single-mode laser designed to operate at a fixed current and wavelength. The drive signal may be modulated by shaping a drive current pulse. The drive signal may be modulated by imposing an RF modulation on a drive current pulse. The drive signal may be further modulated by shaping a drive current pulse.

9 Claims, 11 Drawing Sheets

LASER SPECKLE REDUCTION IN OPHTHALMIC IMAGES, USING CURRENT PULSE-SHAPING

CROSS-REFERENCE TO RELATED APPLICATIONS

This application claims priority to, and the benefit of, U.S. Provisional Patent Application Ser. No. 63/411,235, filed Sep. 29, 2022 and titled "LASER SPECKLE REDUCTION IN OPHTHALMIC IMAGES, USING CURRENT PULSE-SHAPING," which is incorporated by reference herein in its entirety for all purposes.

FIELD

The present disclosure is generally directed to the field of retinal cameras, or fundus imagers. More specifically, it is directed to a retinal imagers using one or more lasers as a light source.

BACKGROUND

Various different types of image-capture devices for imaging a sample under test are known. Of particular interest are imaging systems capable of taking close-up images of a specimen with sufficient detail, e.g., sufficient focus, lighting, magnification, and signal-to-noise ratio (SNR). An example of such an imaging system is a fundus imager (or fundus camera or retinal camera), which is typically used to image the fundus of an eye. The fundus is the interior surface of the eye opposite the eye lens (or crystalline lens) and may include the retina, optic disc, macula, fovea, and posterior pole. Two categories of imaging systems used to image the fundus/retina are flood illumination imagers and scan imagers. Scan imagers may further be divided into confocal point scanning fundus imagers and line scanning imagers.

Flood illumination imagers flood with light an entire field-of-view (FOV) of interest of a specimen at the same time, such as by use of a flash lamp, and capture a full-frame image of the specimen (e.g., the fundus) with a full-frame camera (e.g., a camera having a two-dimensional (2D) photo sensor array of sufficient size to capture the desired FOV, as a whole). For example, a flood illumination fundus imager would flood the fundus of an eye with light, and capture a full-frame image of the fundus in a single image capture sequence of the camera.

FIG. 1 is a conceptual illustration of a flood illumination fundus imager 10. A flash-tube 15 is shown as an illumination source, whose illumination light follows an optical path along illumination axis 17, which may include various system lenses 19, and is folded by mirror 23 onto optical axis 25, which includes system lens 11, to be conveyed to the sample, or specimen, to be imaged (e.g., retina 33 of eye 13 in the present example). System lens 11 is the imager lens closest to the eye 13, and may herein be termed an ocular lens or ophthalmic lens. Optical axis 25 traverses the optical components of the eye 13 (including the cornea 27, iris 28, pupil 29, and crystalline lens 31) to reach the retina 33. Thus, illumination light traveling along optical axis 25 may enter the eye 13 through its cornea 27, pass through its pupil 29, and traverse crystalline lens 31 to flood the retina 33 with light at the back of the eye (e.g., the fundus area), and be scattered by the retina 33 (and other parts of the fundus). Scattered light returning from the fundus may exit through the crystalline lens 31, pupil 29, and cornea 27, and travel along optical axis 25 to a viewing axis 35. Viewing axis 35 may include multiple system lenses 21, and directs the scattered light returning from the fundus to a full-frame camera 37 (e.g., a detector), which includes a 2D photosensitive area. For example, the 2D photosensitive area may be embodied by a 2D sensor array of photosensitive elements (e.g., photocells, photodiodes, phototransistors, etc.). The entire field-of-view (FOV) 38 of the fundus is captured as a whole by the 2D sensor array to produce a full-frame image 39 of the fundus of the eye 13. Since viewing axis 35 and illumination axis 17 are coincident along optical axis 25, mirror 23 typically has a centrally located aperture 43 used to permit scattered light returning from eye 13 to pass through mirror 23 onto viewing axis 35 to be captured by camera 37. Mirror 23 may be flat and annular (e.g., ring-shaped) with round aperture 43 at its center. Mirror 23 may further be imaged to the pupil 29 if it is used for pupil splitting.

Pupil splitting permits illumination light (light entering the eye 13) and returning light (scattered light exiting the eye) to follow different paths into and out of the eye 13, at optimally chosen regions of the pupil. These regions may be chosen, for example, to avoid pupil clipping (e.g., avoid part of the light from being blocked/clipped by the iris 28 whose center defines the pupil 29), light scattering due to cataracts (e.g., clouded regions of the crystalline lens 31), and specular reflections (e.g., reflexes) from the cornea 27, such as due to the illumination light. To ease implementation of pupil splitting, mirror 23, which reflects illumination light towards the eye 13 and whose aperture 43 permits passage of returning light to the camera 37, may be imaged to (e.g., be on conjugate plane with), or near, the pupil 29. For example, when mirror 23 folds (e.g., reflects) illumination light from illumination axis 17 onto optical axis 25 towards eye 13, an annular-shape illumination region (or illumination ring) may be created at the eye 13 (e.g., near the pupil 29) due to the mirror's rounded aperture 43. That is, round aperture 43 of mirror 23 may create a round, non-illuminated region near the cornea 27 at the center of the annular-shape illumination region. Scattered light may exit the eye 13 through this non-illuminated region and thereby avoid illumination light entering the eye 13.

Another source of image artifacts are reflexes (e.g., light reflections) at various system lenses. For example, reflex artifacts at the ophthalmic lens 11 created by the illumination light as it passes through ophthalmic lens 11 can be of particular concern. Such specular artifacts from system optical surfaces may be reduced by using so-called dark spots, which are stationary in illumination paths and carefully positioned to prevent certain surface areas of system optics from being illuminated. Eliminating reflexes may place constraints on the system which may limit its FOV. An example of a flood illumination imaging system is found in U.S. Pat. No. 3,915,564, assigned to the same assignee as the present disclosure, and herein incorporated in its entirety by reference.

By contrast, a confocal point scanning fundus imager uses a coherent point beam of light, such as a laser, that is scanned both vertically and horizontally across a desired FOV of a sample (e.g., the fundus), and image-captures one point-illuminated portion, or spot, of the fundus at a time. That is, the desired, full FOV is not captured as a whole in a single image capture sequence of a camera. Rather, as the point beam is scanned across the sample, illuminating a different point of the sample at each scanning step, the returning (e.g., refracted or reflected) light passes through a pinhole to reach a single, predefined location on a photodetector that captures a point-portion (e.g., a pixel of image data) of the sample at a time (e.g., at each scanning step). The pinhole helps to eliminate out-of-focus light signal by allowing only the center of the returning light beam to reach the photodetector (e.g., the outer, diffused portion of the returning light beam is blocked). The returning light reaches the same point-location on the photodetector (e.g., of a charged coupled device, CCD, camera) irrespective of scan position of the scanning point beam on the sample, and many individual point-portions (e.g., pixels of image data) are captured in sequential image capture sequences of a camera to create a full frame image. The many, captured point-portions resulting from one full scan of the desired FOV of the sample are combined to create a composite image, which may constitute a full-frame image.

FIG. 2 illustrates a simplified, exemplary scanning pattern of a confocal point scanning fundus imager. It is to be understood that other scanning patterns, such as circular or spiral patterns, are possible. In the present, illustrative example, each point (e.g., point-illuminated portion) Sp_1 to Sp_n is captured separately and individually in a scanning pattern. Since only one point in the sample is illuminated and captured at a time, imaging typically includes scanning over a regular raster (e.g., a rectangular pattern of parallel scanning rows of spots) on the sample, e.g., the fundus. For example, a laser point beam may be scanned across the sample in an X-Y plane (perpendicular to a primary axial direction (e.g., Z-axis) of the point beam) by using one or more scanning components (e.g., servo controlled rotating, or oscillating, mirrors, or galvanometers). For example, a separate row (e.g., R1 to Rm) of points may be captured in corresponding separate horizontal scans, H-scan, one after another, and the scanning point beam may be scanned vertically in one-row-offset incremental steps (e.g., one vertical step after each horizontal scan) to define a vertical scan, V-scan. Typically, slower scans may provide a better signal-to-noise ratio, resulting in better contrast and higher resolution.

Due to the point confocal arrangement of illumination and detection, the confocal point scanning fundus imager may advantageously suppress stray-light and out-of-focus light, and thereby produce high contrast images without the need for pupil splitting. Thus, a benefit of the confocal point scanning fundus imager over the flood illumination fundus imager is an increased level of confocality, which provides greater discrimination against undesirable light scattered from surfaces other than the target point to be imaged. However, since the confocal point scanning fundus imager operates with point illumination, it may include high intensities which raise safety issues when imaging a retina. Similarly, since much of the returning light from the sample is blocked by the pinhole leading to the photodetector, its increased resolution is generally at the cost of decreased signal intensity so that its exposure time may be elongated. Additionally, the confocal point scanning fundus imager generally includes multiple scanning components (e.g., multiple galvanometers, or galvos) to achieve horizontal and vertical scans, which can be expensive and complicated, and can slow their image production since many points are collected to construct a full-frame composite image. This also may raise issues of eye movement during the collection of an image, which may lead to image distortion.

A line scanning imager (e.g., a laser-line scanning imager or broad-line scanning imager) may be thought of as a combination of a confocal point scanning imager and a flood illumination imager. A line scanning imager illuminates a linear region of a sample (e.g., the retina) at a time. The linear strip may simultaneously illuminate, for example, a length-span extending from a left-most boundary of a desired FOV to the right-most boundary of the FOV, or equivalently, extending from a top-most boundary of the desired FOV to the bottom-most boundary of the FOV. The scan line may be scanned (e.g. traversed) across the sample (e.g. vertically or horizontally), and thereby illuminates the entire FOV in one sweep, in a piecemeal fashion. The camera (or detector) of the line scanning imager captures one strip-portion of the sample at a time, which may then be combined/montaged to create a composite full-frame image.

In the above discussion, a laser light source (such as a laser diode) may be used to provide the coherent light beam that illuminates the sample/retinal. A difficulty of using laser diodes is that they are typically tuned to a single wavelength of operation, leading them to be prone to producing speckle (a granular noise texture) that degrades the quality of the captured image. It has been found that speckle can be reduced by varying the scanning wavelength, such as by use a tunable laser, which has an output wavelength that can be altered in a controlled manner. Tunable lasers, however, are much less cost effective for retinal camera applications than laser diodes that are tuned to a single wavelength.

A need exists to provide a retinal camera/fundus imager with a laser diode that produces images of reduced speckle noise.

A need exists to provide a driving mechanism/method for driving a laser diode synchronized to the sensor integration time of a photodetector/image sensor/(digital) camera in such a manner so as to reduce the production of speckle noise in a captured image.

SUMMARY

An eye imaging system configured for producing images with reduced speckle artifacts is disclosed. In various embodiments, system may comprise, for example, a laser diode configured for providing a beam of radiation to the eye; a detector configured for collecting light returning from the eye and generating output signals in response thereto, the detector having a sensor integration time; a driver circuit configured for applying a modulated drive signal to the laser diode, the modulated drive signal configured for inducing a spectral broadening of the beam of radiation during the sensor integration time.

In various embodiments, the laser diode may be a single-mode laser designed to operate at a fixed current and wavelength. The drive signal may be modulated by shaping a drive current pulse. The drive signal may be modulated by imposing an RF modulation on a drive current pulse. The drive signal may be further modulated by shaping a drive current pulse.

Other objects and attainments together with a fuller understanding of this disclosure will become apparent and appreciated by referring to the following description and claims taken in conjunction with the accompanying drawings.

Several publications may be cited or referred to herein to facilitate the understanding of this disclosure. All publications cited or referred to herein, are hereby incorporated herein in their entirety by reference.

The embodiments disclosed herein are only examples, and the scope of this disclosure is not limited to them. Any embodiment feature mentioned in one claim category, e.g. system, can be claimed in another claim category, e.g. method, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

In the drawings wherein like reference symbols/characters refer to like parts.

DETAILED DESCRIPTION

A general discussion of a typical fundus imaging system, or retinal camera, is provided below in reference to FIG. 13. As is explained below various types of light sources may be used. Of particular interest of this disclosure is the use of a laser light source, such as for example, a laser diode. As is explained more fully below, this disclosure may be use in an imaging system configured to use a laser system (e.g., laser diode(s)) that are tuned to operate at a single wavelength (e.g., a single mode laser diode). Before delving into some issues addressed in this disclosure, it may be helpful to provide a general discussion of a typical digital camera, such as suitable for use in a retinal camera system in accord with this disclosure.

Figure 1:
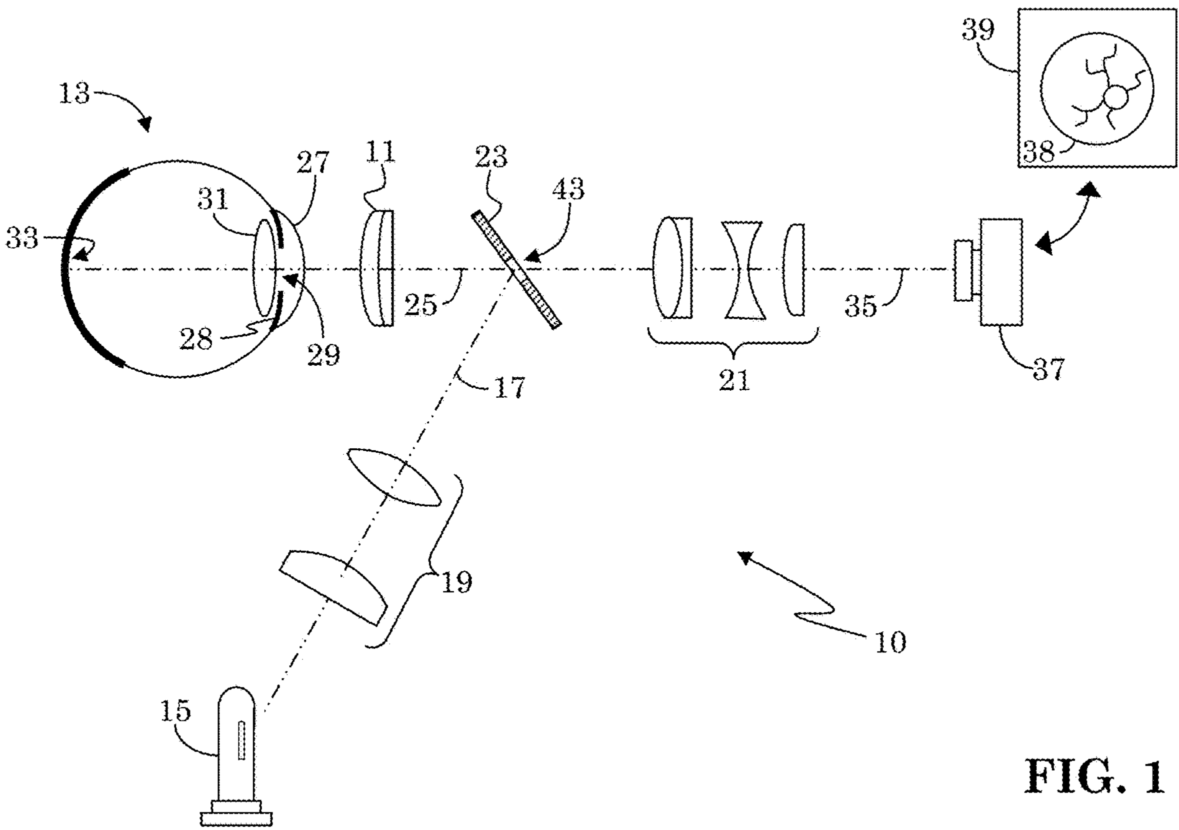
FIG. 1 is an exemplary conceptual illustration of a flood illumination fundus imager.
Figure 2:
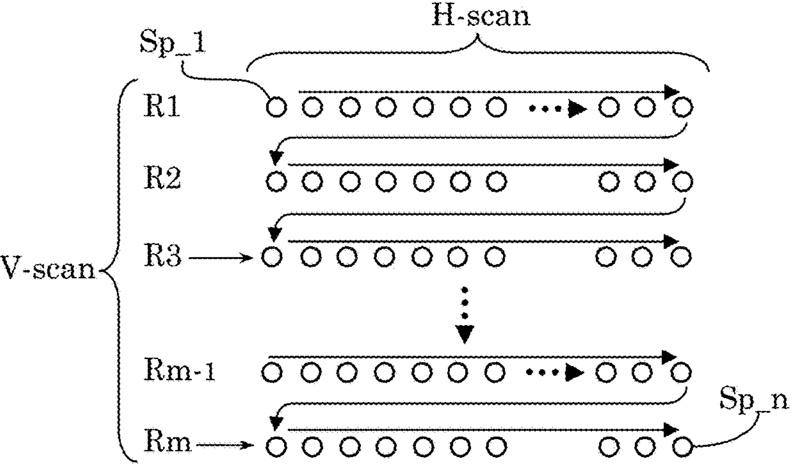
FIG. 2 illustrates a simplified, exemplary scanning pattern for a confocal point scanning fundus imager.
Figure 3:
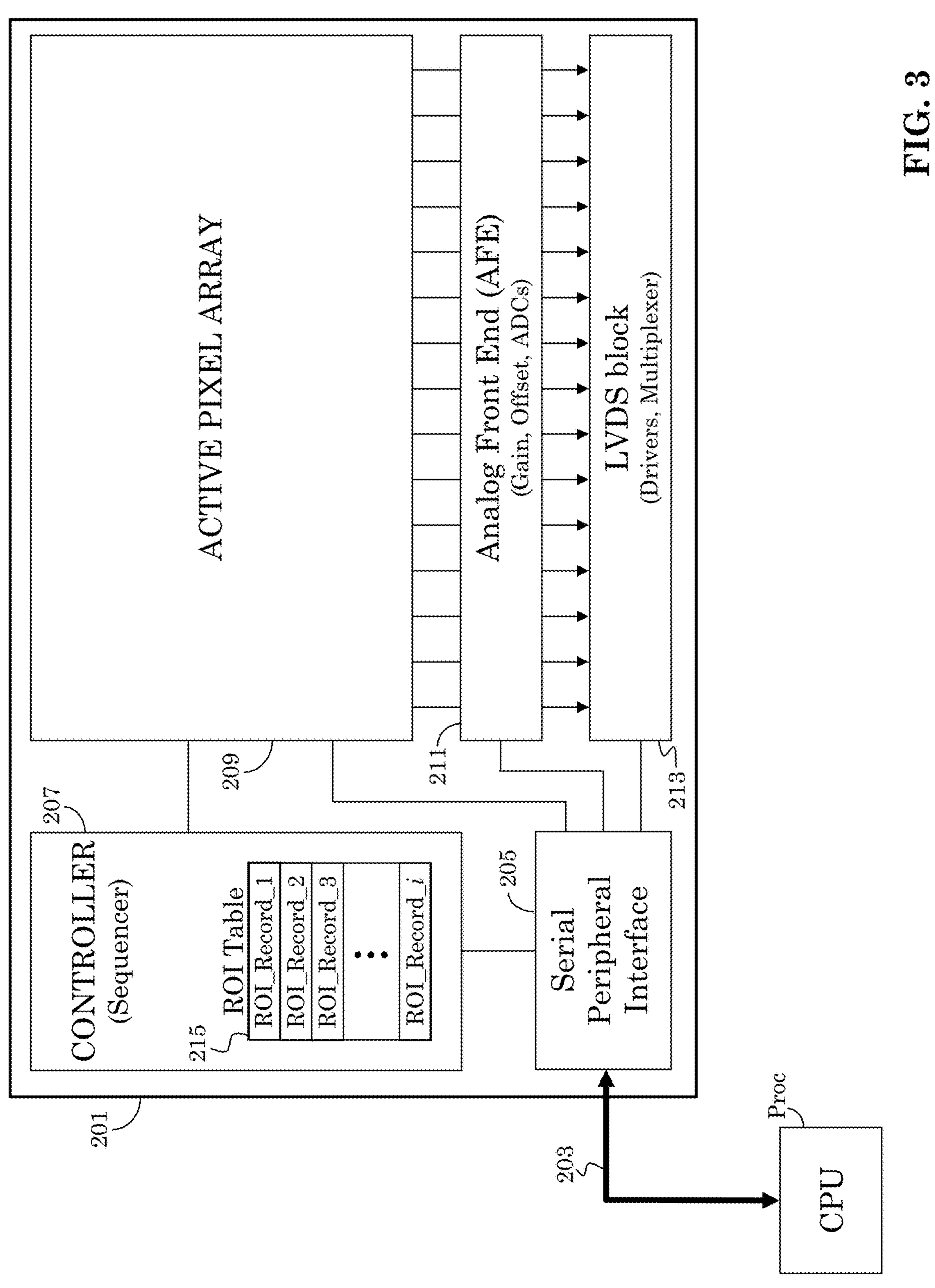
FIG. 3 illustrate an exemplary internal structure of a camera (photosensor imaging system), in accordance with various embodiments.

FIG. 3 illustrates an exemplary internal structure of a typical (digital) camera 201 in accord with this disclosure. As shown, a CPU (or computing device or computer system or data processor) Proc (such as processor Proc in FIG. #B) may communicate with camera 201 by means of a communication link 203, such as a USB® or CameraLink® serial communication link. Internally, communication to/from CPU Proc may be handled by a Serial Peripheral Interface (SPI) block 205, or other appropriate communication interface. SPI is a synchronous serial communication interface specification commonly used in industry for short distance communication, primarily in embedded systems, and may be used in some digital cameras. Internally, SPI block 205 may relay communications between multiple internal component blocks. For example, SPI block 205 may relay instructions received from CPU Proc to a controller (or sequencer) 207, whose function may be to control the operation of an active pixel array (e.g., image sensor or sensor or sensor array) 209. That is, sequencer 207 may generate the necessary signals for image acquisition. The image is captured by active pixel array (or sensor) 209, which may be a global shutter array or a rolling shutter array. Sensor 209 may support one or more regions of interest (ROIs), as defined by use of one or more ROI-definition records (e.g., registers). Internally, sensor 209 may consist of a 1D or 2D array of photosensitive elements (e.g., pixels), and integrates photonic energy received at a region of interest within the 1D or 2D array, as defined by a specific ROI entry. That is, the controller 207 may control the exposure duration of the sensor 209 (period of sensor integration), such as by use of a Start-Exposure signal and a Stop-Exposure signal. For example, an executable program (e.g., executed within a processing unit, controller, or state machine) on the camera may set the exposure time, and issue the Start-Exposure signal (e.g. send a signal pulse to the sensor 209) to start exposure of an ROI (e.g., pixels within the ROI), and the camera controller may issue the Stop-Exposure signal (e.g., send a signal pulse to the sensor 209) when the previously set exposure time elapses/ends. The time between issuance of the Start-Exposure signal and issuance of the Stop-Exposure signal may thereby define the exposure duration of the sensor 209, e.g., set the period of sensor integration (e.g., pixel exposure time) during which the photosensitive elements of sensor 209 are exposed to incoming light and permitted to reach a final state of sensed photonic energy (e.g., signal information). The final states of photonic energy of the pixels the pixels within a selected ROI may be captured by being transferred to an analog front end (AFE) block 211, where the captured signal data from each pixel may be amplified (e.g., by use of a column amplifier block) and converted to digital form (e.g., by use of a column analog-to-digital converter (ADC) block). As it would be understood, it takes time for the pixel information to be transferred, captured, and conditioned by AFE block 211 in preparation for the image data to be read out. This time may be part of a time delay between the end of sensor integration (e.g., pixel exposure time) and the start of sensor readout, which may be part of the Frame-Overhead-Time, FOT. The captured pixel information may then be read out by using appropriate output drivers using a suitable communication protocol. Although not critical to this disclosure, in the present example, the camera uses low voltage differential signaling, LVDS, (a high speed, serial communication protocol). Thus, during a read phase, image data from AFE block 211 is passed to an LVDS block 213, which may output the captured pixel information to an external component, such as CPU 203. Additional information of the operation of a typical camera suitable for use in retinal imager may be found in U.S. Pat. No. 11,153,463, herein incorporated in its entirety by reference.

Figure 4:
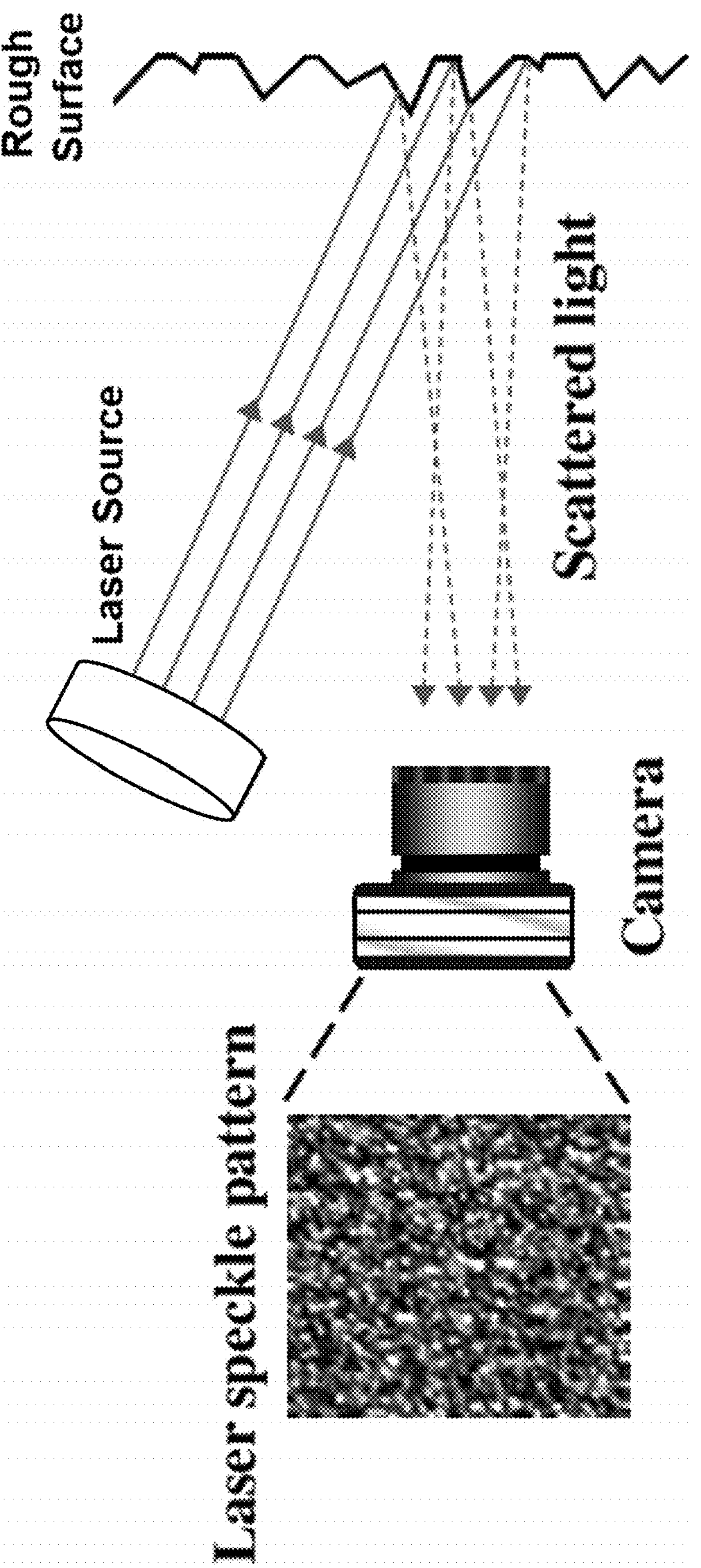
FIG. 4 illustrates an exemplary generation of speckle in a typical retinal camera, in accordance with various embodiments.

Returning to the topic of the present application, speckle is an interference effect, caused by the mutual interference of coherent or partially-coherent wavefronts. In imaging applications where light sources with a high degree of temporal coherence (such as lasers) are used, speckle results in a "grainy" effect that degrades image contrast. FIG. 4 illustrates the generation of speckle in a typical retinal camera using a laser source. Speckle can be reduced by diversification of one or more optical parameters, including wavelength, polarization, and numerical aperture. A discussion of this approach may be found in Trisnadi, Jahja I. "Speckle contrast reduction in laser projection displays", Projection displays VIII. Vol. 4657. International Society for Optics and Photonics, 2002, and in Schmitt, Joseph M., S. H. Xiang, and Kin Man Yung. "Speckle in optical coherence tomography." Journal of biomedical optics 4.1 (1999): 95-105. In the case of laser diodes, it has been found that modulation of the laser drive current can be an effective means of introducing wavelength diversity (through thermal tuning, mode-hopping, or a combination of both), such as discussed in Yilmazlar, Ismail, and Metin Sabuncu. "Speckle noise reduction based on induced mode hopping in a semiconductor laser diode by drive current modulation." Optics & Laser Technology 73 (2015): 19-22.

The CLARUS™ is product line of retinal cameras (e.g., fundus imagers) from Carl Zeiss Inc™ product line uses infrared laser diodes for its infrared preview and capture modes; these images are afflicted by speckle. It is to be understood that other laser diodes in other frequency ranges (e.g., white and/or color spectrum) could similarly be afflicted with speckle, and the present disclosure would apply equally to reduce speckle in lasers in general, and laser diodes in particular, such as single mode laser diodes. Thus, this disclosure aims to mitigate this problem by reducing the impact of speckle by way of electronically shaping the current pulse supplied to the laser, e.g., without necessarily resorting to overdriving the laser, which can reduce the effective lifespan of the laser.

Figure 5:
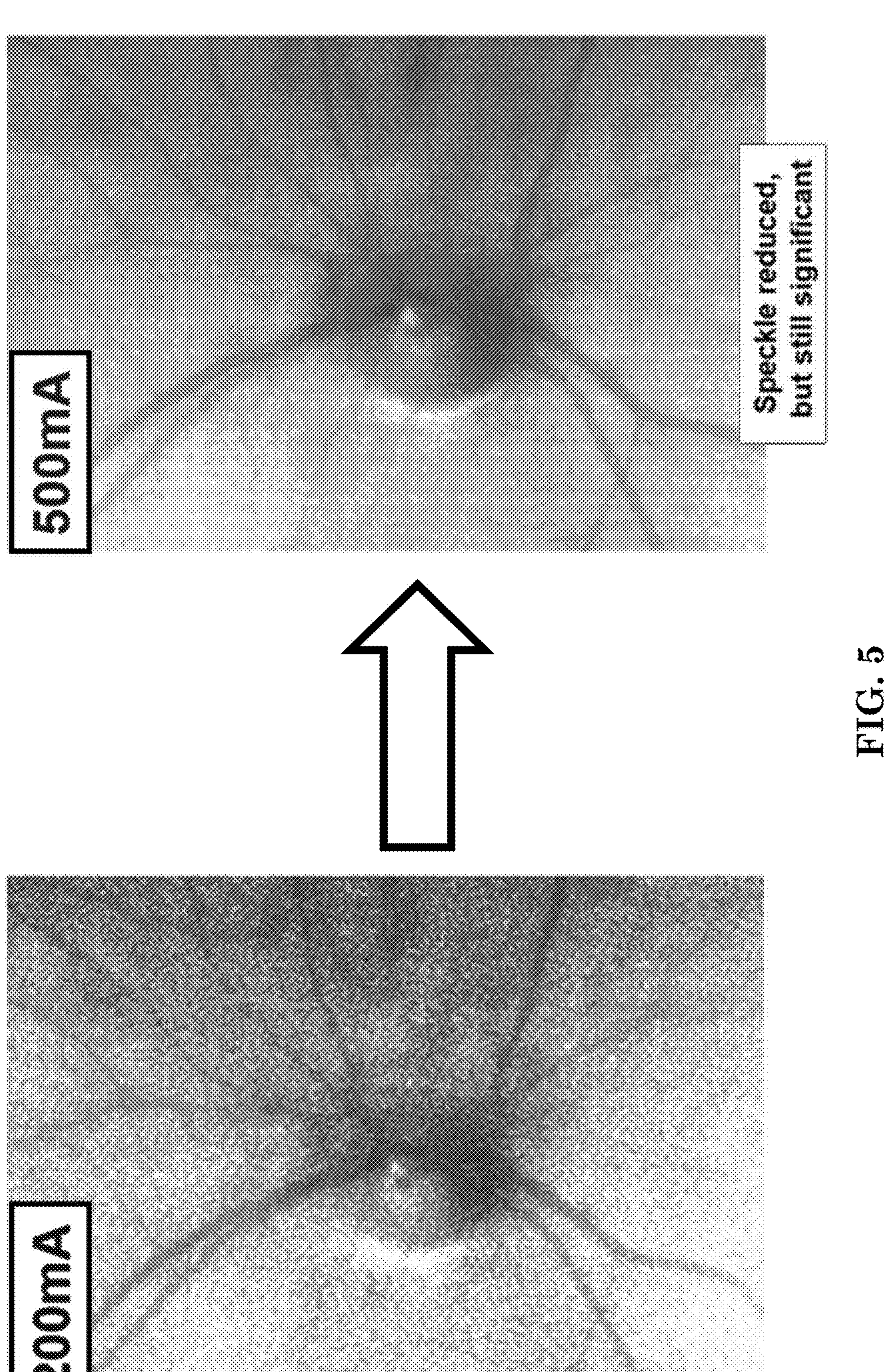
FIG. 5 illustrates an exemplary method of reducing speckle by overriding a laser diode, in accordance with various embodiments.

For example, FIG. 5 illustrates a method of reducing speckle by overriding a laser diode. Previously an earlier model of the CLARUS™ family, e.g., the CLARUS 500™, speckle was mitigated by overdriving the infrared laser diodes with a current of about 500 mA (instead of the laser's maximum rated drive current 275 mA). This overdriving effect was found to reduce speckle significantly. More recently, however, it was found that overdriving the laser diode may be leading to an unacceptably high level of failures of infrared lasers in the field. After extensive in-house testing, the root-cause of these failures was found to be the excess drive current. Therefore, overdriving may not be an optimal method for mitigation of speckle.

This disclosure includes a more sustainable method for mitigating speckle without ill-affecting the lifespan of a laser diode. This disclosure comprises an electronic driving scheme for laser diodes that reduces speckle in the output image through variation of the laser diode's output wavelength during the camera's image exposure time. Variation of the laser diode's output wavelength may be induced by any of: Thermal tuning and/or mode-hopping achieved via shaping of the drive current pulse; Mode-hopping, achieved via radio frequency (RF) modulation of the laser drive current pulse; and/or a combination of those features.

Variation of the laser wavelength results in a changing speckle pattern that is temporally averaged by the camera' photosensor (e.g., "sensor"), effectively reducing the overall speckle contrast. Thus, unlike the prior art, this disclosure uses electronic current pulse-shaping specifically for the purpose of reducing speckle in ophthalmic imaging applications. The present approach also uses the combination of current pulse shaping with high-frequency modulation in order to generate wavelength diversification for the purpose of speckle reduction.

Prior methods aimed at reducing speckle in direct optical imaging have suggested using moving diffuser plates, scanning devices, or using incoherent sources, as described, for example in Mehta, Dalip Singh, et al. "Laser speckle reduction by multimode optical fiber bundle with combined temporal, spatial, and angular diversity." Applied optics 51.12 (2012): 1894-1904, and in Trisnadi, Jahja I. "Speckle contrast reduction in laser projection displays." Projection displays VIII. Vol. 4657. International Society for Optics and Photonics, 2002. But such approaches are more complicated and often include additional, or more expensive, components.

Unlike prior art proposed solutions, this disclosure has the advantage of being a low cost and low complexity solution. The present approach can be implemented as a purely electronic method with no additional mechanical or optical elements/components required. Additionally, since the solution is an electronically controlled drive current pulse of specific shape and frequency, the amount of speckle reduction can be electronically controlled by switching pulse shapes and/or altering the applied drive frequency. This permits this disclosure to control/adjust the degree of speckle reduction, such as to mitigate/limit the risk of damage to the (laser) diode. That is, the amount of achieved speckle reduction can be customized to the characteristics/limitations of the specific diode being used. For example, total achievable wavelength shift for a GaAs diode may be a few tens of nm, the amount that can be achieved without attrition might be significantly less.

Figure 6:
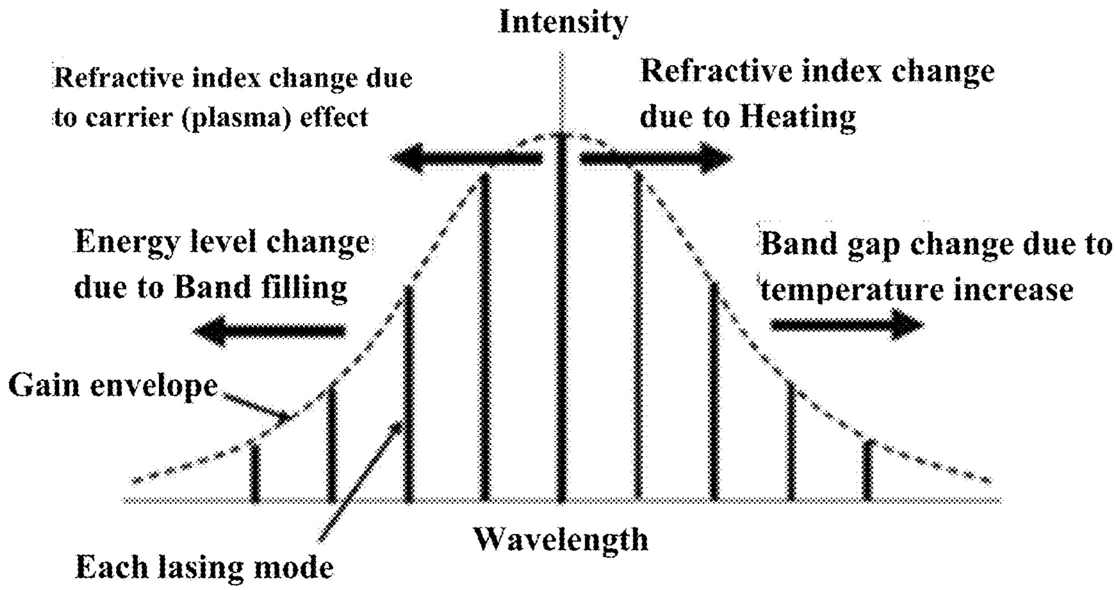
FIG. 6 illustrates how heating/cooling a (single mode) laser diode can induce physical effects that alter its operating optical wavelength, in accordance with various embodiments.

FIG. 6 illustrates how heating/cooling a (single mode) laser diode can induce physical effects that alter its operating optical wavelength. A single-mode laser is designed to operate at a constant current and provide a very narrow spectrum at a fixed wavelength. However, heating/cooling the laser diode can induce physical effects that alter its optical wavelength, as shown in FIG. 6.

The goal of this disclosure is to electronically excite one or more of these physical effects in order to generate variation in the laser diode's wavelength during a single exposure interval (sensor integration time). For CLARUS™ infrared reflectance imaging, these exposure intervals, or sensor integration times, are on the order of 20-200 microseconds. During each exposure interval, a driver circuit applies a drive current to the laser diode (or diode laser). At the end of the exposure interval (sensor integration time), the current is switched off for a time, while the image data is read from the image sensor, as discussed above in reference to FIG. 3. In applications where a series of exposures are taken in a fast sequence, this on/off action of the laser diode resembles pulsing. Hereafter, the laser's current action during a single exposure may be referred to as a 'pulse'.

This disclosure provides a temporally-shaped pulse of (e.g., drive) current that causes variations in the output wavelength of the diode laser. These variations may be provoked, for example, through thermal tuning, induced by shaping of the laser drive current pulse (GaAs diodes tune by about +0.3 nm/° C.); RF modulation of the laser current (which likely creates wavelength instability through "mode hops"); and/or a combination of these features.

The change of wavelength leads to a change in the speckle pattern, and the resulting diversity in the speckle pattern within the integration time of the sensor leads to a reduction in speckle contrast overall.

Figure 7:
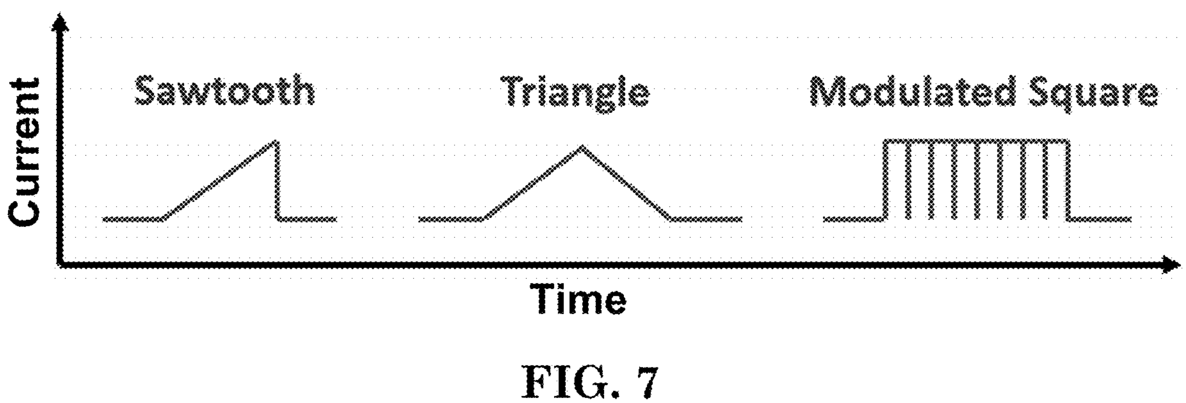
FIG. 7 illustrates some exemplary pulse-shaping schemes for the driving current of a laser diode, in accordance with various embodiments.

FIG. 7 illustrates some pulse-shaping schemes for the driving current of a laser diode, in accordance with the various embodiments. A number of different pulse-shaping schemes can be used including, for example, sawtooth pulse, triangle pulse and/or high-frequency modulated square pulse.

The pulse-shaping may be realized through an arbitrary waveform generator, or through custom-designed analog electronics.

Figure 8:
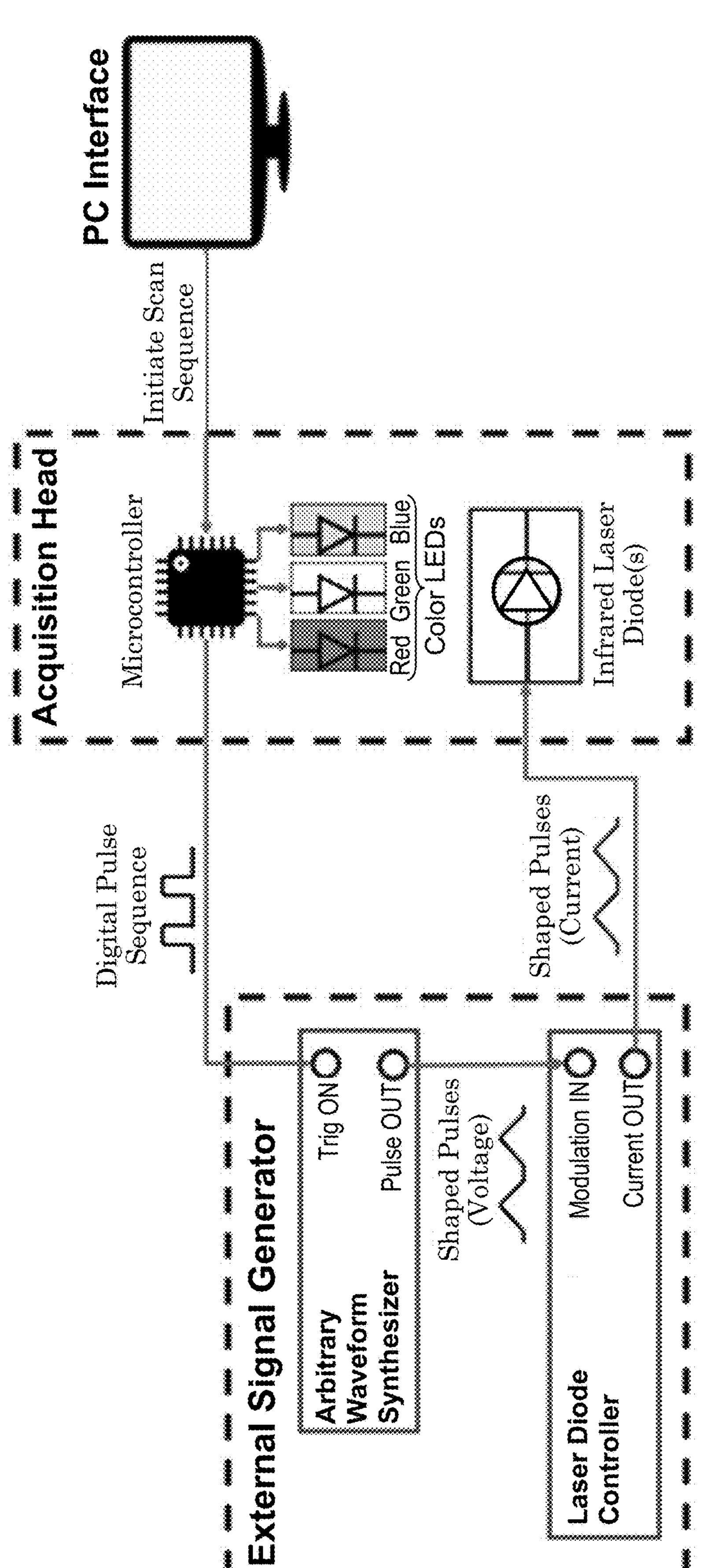
FIG. 8 is an exemplary system schematic of a prototype setup for arbitrary shaping of laser pulse waveform, in accordance with various embodiments.

FIG. 8 is a system schematic of a prototype setup for arbitrary shaping of laser pulse waveform in accord with this disclosure. Color LEDs are driven by on-board electronics (as in the CLARUS product line), while the laser diode(s) are driven by routing the control signals through an external signal generator. For infrared reflectance modes, ordinarily in the CLARUS product line current pulses are supplied to the infrared lasers via on-board electronics. However, in the prototype these current pulses are supplied from an external signal generator module, incorporating an arbitrary waveform synthesizer and a laser diode current controller, as shown in FIG. 8. The external signal generator is fully or partially enclosed in a housing, so as to prevent incidental adjustment of the on-board controls. In order to drive both of the laser diodes in the acquisition head simultaneously for mydriatic scan modes, a second external signal generator may be used.

Figure 9:
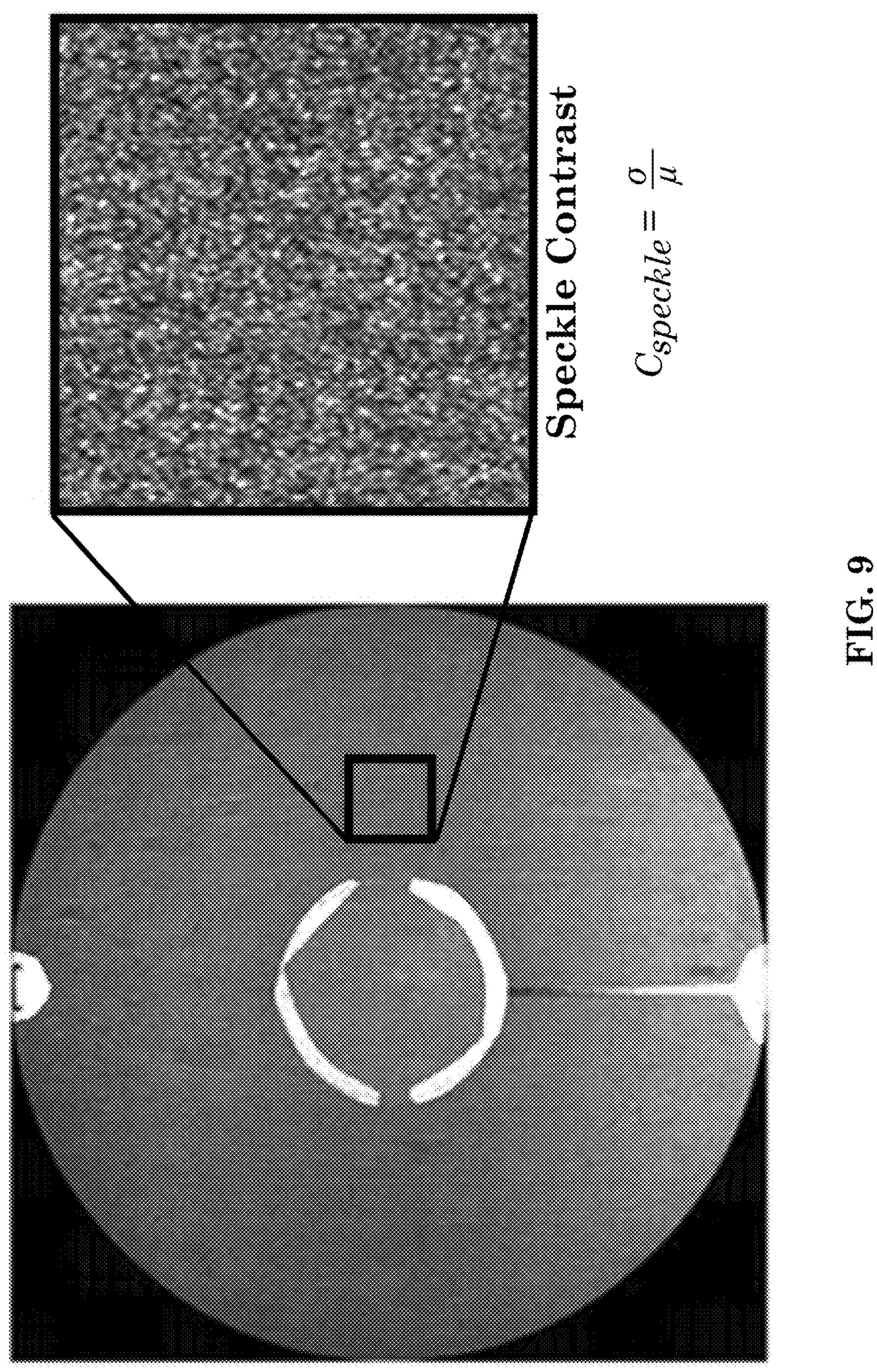
FIG. 9 provides an exemplary method for measuring speckle contrast, in accordance with various embodiments.

Results from prototype tests were compiled by measuring speckle contrast on a paper test target. FIG. 9 provides an example of a method for measuring speckle contrast. Speckle contrast is a dimensionless measure of the impact of speckle, as is explained in Tumlinson, Alexandre R., Nathan Shemonski, and Yuan Liu. "Interferometry with pulse broadened diode laser." U.S. Pat. No. 10,495,439. 3 Dec. 2019, herein incorporated in its entirety by reference for all purposes.

Figures 10, 11:
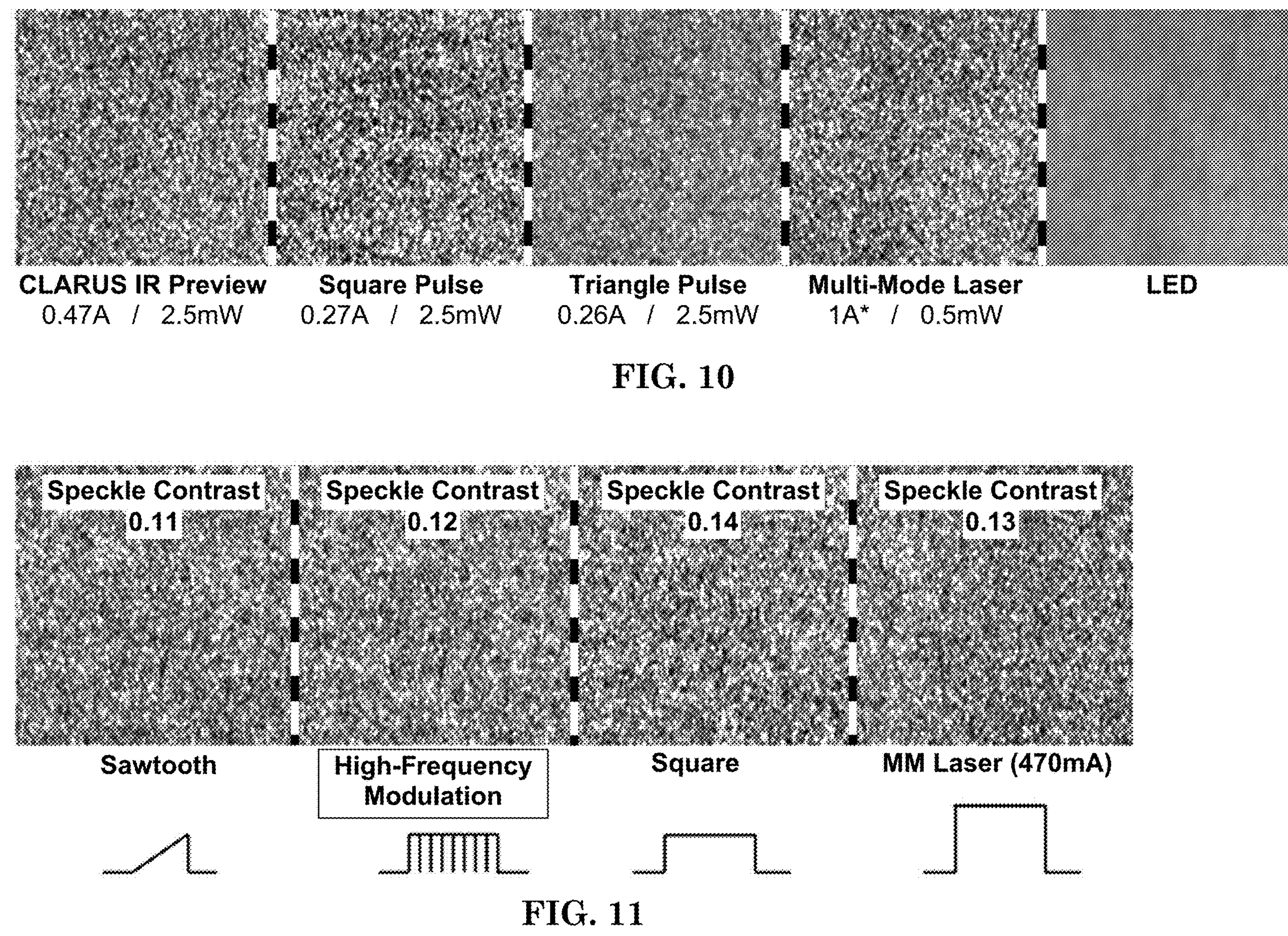
FIG. 10 and FIG. 11 show exemplary visualization of speckle on a normalized scale, in accordance with various embodiments.

The results indicate that the shaped pulse waveforms deliver reduced speckle contrast, when compared to a simple square pulse. FIGS. 10 and 11 visualize speckle on a normalized scale.

Figure 12:
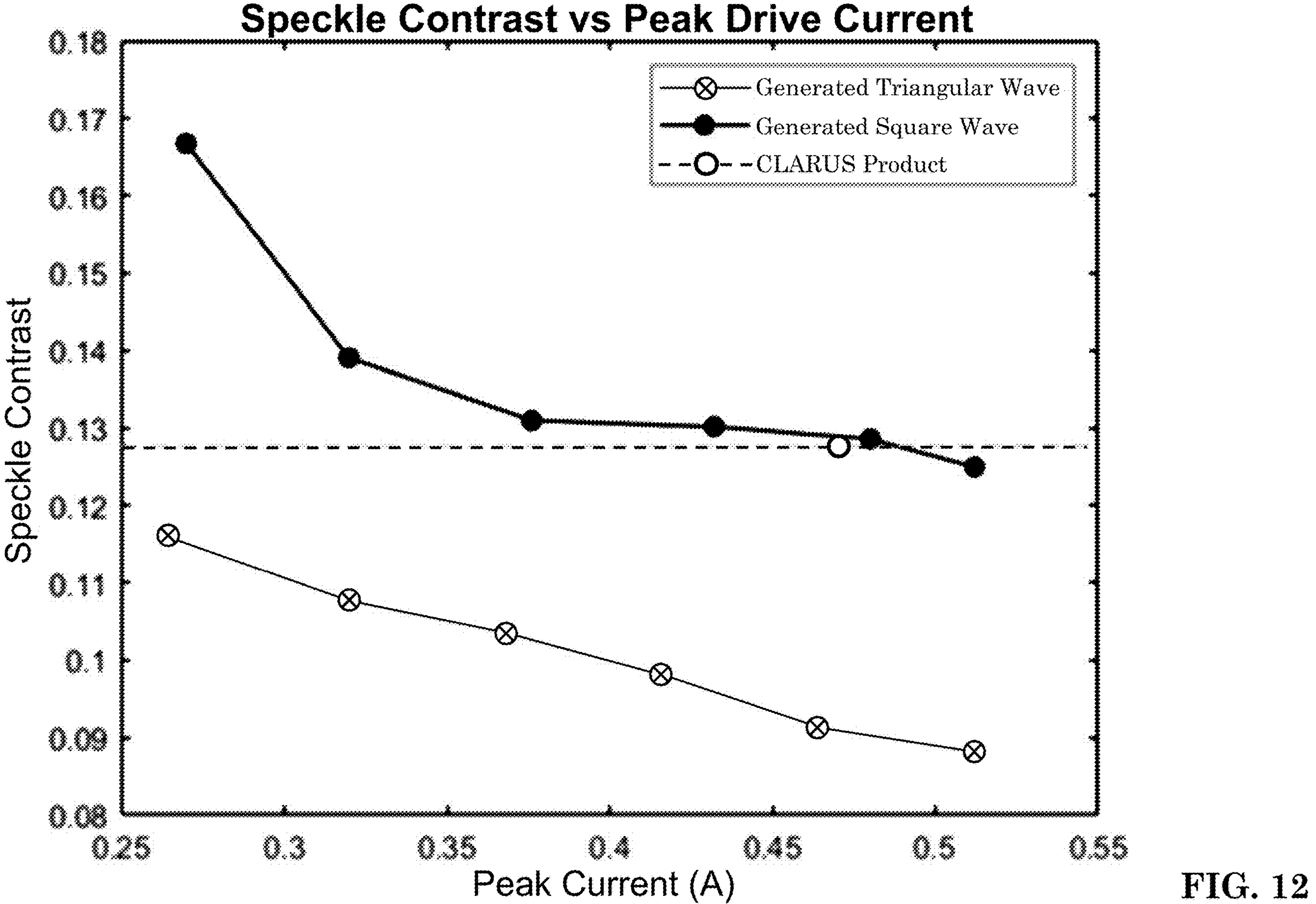
FIG. 12 demonstrates that the disclosure achieves improvements compared to an over-driven square pulse scheme (such as used in CLARUS product, for example) without exceeding the laser diode's rated current of 275 mA, in accordance with various embodiments.

FIG. 12 is a plot comparing the use of a generated triangular wave and a generated square wave to the overdriving approach used in the CLARUS line of retinal cameras. As shown, Improvement is also seen compared to the over-driven square pulse scheme that is currently in the CLARUS product line, without exceeding the laser diode's rated current of 275 mA.

Hereinafter is provided a description of various hardware and architectures suitable for this disclosure.

Two categories of imaging systems (e.g., retinal cameras) used to image the fundus are flood illumination imaging systems (or flood illumination imagers) and scan illumination imaging systems (or scan imagers). Flood illumination imagers flood with light an entire field of view (FOV) of interest of a specimen at the same time, such as by use of a flash lamp, and capture a full-frame image of the specimen (e.g., the fundus) with a full-frame camera (e.g., a camera having a two-dimensional (2D) photo sensor array of sufficient size to capture the desired FOV, as a whole). For example, a flood illumination fundus imager would flood the fundus of an eye with light, and capture a full-frame image of the fundus in a single image capture sequence of the camera. A scan imager provides a scan beam that is scanned across a subject, e.g., an eye, and the scan beam is imaged at different scan positions as it is scanned across the subject creating a series of image-segments that may be reconstructed, e.g., montaged, to create a composite image of the desired FOV. The scan beam could be a point, a line, or a two-dimensional area such a slit or broad line. Examples of fundus imagers are provided in U.S. Pat. Nos. 8,967,806 and 8,998,411.

Figure 13:
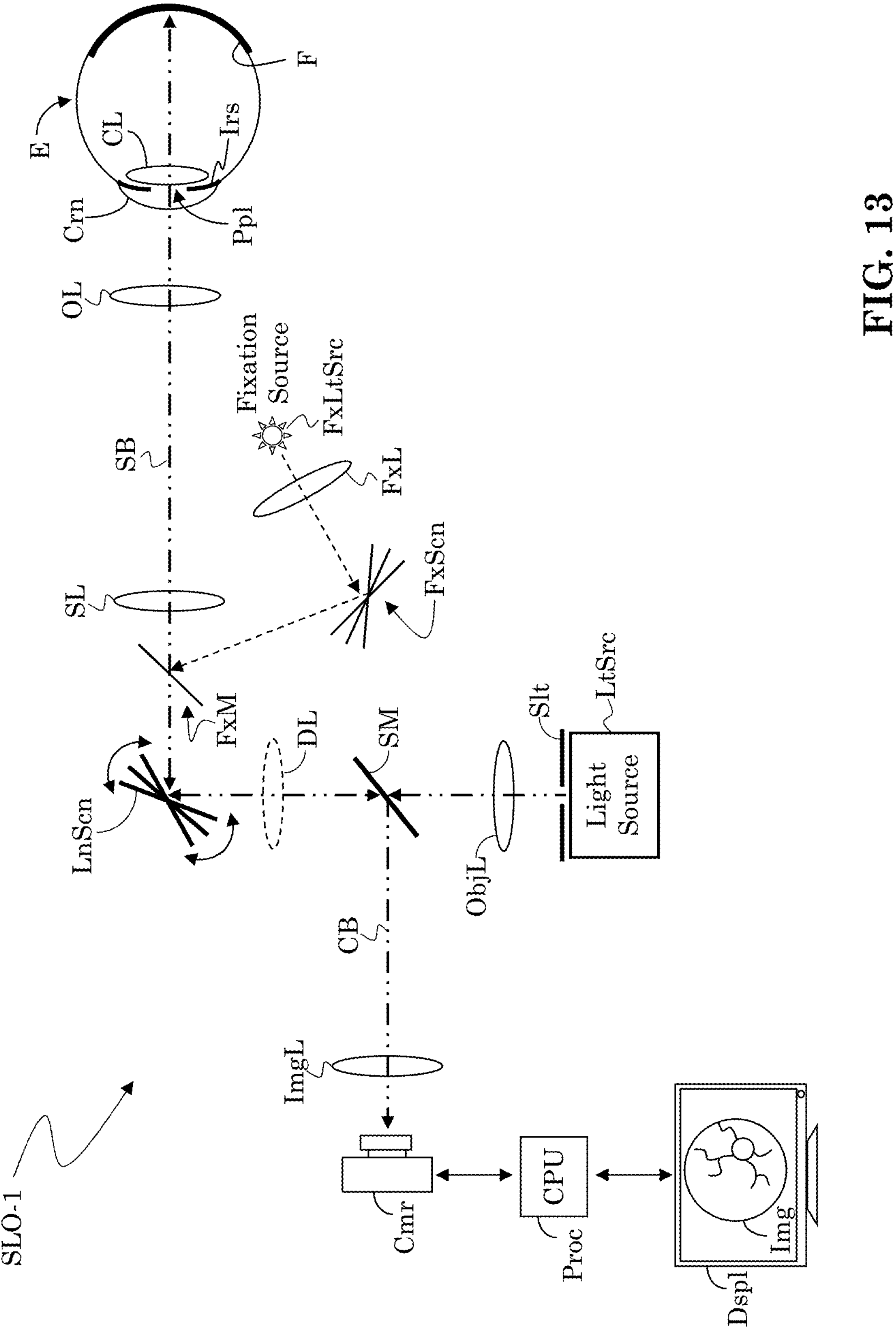
FIG. 13 illustrates an example of a slit scanning ophthalmic system (or retinal camera) for imaging a fundus, in accordance with various embodiments.

FIG. 13 illustrates an example of a slit scanning ophthalmic system SLO-1 for imaging a fundus F, which is the interior surface of an eye E opposite the eye lens (or crystalline lens) CL and may include the retina, optic disc, macula, fovea, and posterior pole. In the present example, the imaging system is in a so-called "scan-descan" configuration, wherein a scanning line beam SB traverses the optical components of the eye E (including the cornea Crn, iris Irs, pupil Ppl, and crystalline lens CL) to be scanned across the fundus F. In the case of a flood fundus imager, no scanner is needed, and the light is applied across the entire, desired field of view (FOV) at once. Other scanning configurations are known in the art, and the specific scanning configuration is not critical to this disclosure. As depicted, the imaging system includes one or more light sources LtSrc, preferably a multi-color LED system or a laser system (e.g., laser diode(s)) in which the etendue has been suitably adjusted. An optional slit Slt (adjustable or static) is positioned in front of the light source LtSrc and may be used to adjust the width of the scanning line beam SB. Additionally, slit Slt may remain static during imaging or may be adjusted to different widths to allow for different confocality levels and different applications either for a particular scan or during the scan for use in suppressing reflexes. An optional objective lens ObjL may be placed in front of the slit Slt. The objective lens ObjL can be any one of state-of-the-art lenses including but not limited to refractive, diffractive, reflective, or hybrid lenses/systems. The light from slit Slt passes through a pupil splitting mirror SM and is directed towards a scanner LnScn. It is desirable to bring the scanning plane and the pupil plane as near together as possible to reduce vignetting in the system. Optional optics DL may be included to manipulate the optical distance between the images of the two components. Pupil splitting mirror SM may pass an illumination beam from light source LtSrc to scanner LnScn, and reflect a detection beam from scanner LnScn (e.g., reflected light returning from eye E) toward a camera Cmr. A task of the pupil splitting mirror SM is to split the illumination and detection beams and to aid in the suppression of system reflexes. The scanner LnScn could be a rotating galvo scanner or other types of scanners (e.g., piezo or voice coil, micro-electromechanical system (MEMS) scanners, electro-optical deflectors, and/or rotating polygon scanners). Depending on whether the pupil splitting is done before or after the scanner LnScn, the scanning could be broken into two steps wherein one scanner is in an illumination path and a separate scanner is in a detection path. Specific pupil splitting arrangements are described in detail in U.S. Pat. No. 9,456,746, which is herein incorporated in its entirety by reference.

From the scanner LnScn, the illumination beam passes through one or more optics, in this case a scanning lens SL and an ophthalmic or ocular lens OL, that allow for the pupil of the eye E to be imaged to an image pupil of the system. Generally, the scan lens SL receives a scanning illumination beam from the scanner LnScn at any of multiple scan angles (incident angles), and produces scanning line beam SB with a substantially flat surface focal plane (e.g., a collimated light path). Ophthalmic lens OL may then focus the scanning line beam SB onto an object to be imaged. In the present example, ophthalmic lens OL focuses the scanning line beam SB onto the fundus F (or retina) of eye E to image the fundus. In this manner, scanning line beam SB creates a traversing scan line that travels across the fundus F. One possible configuration for these optics is a Kepler type telescope wherein the distance between the two lenses is selected to create an approximately telecentric intermediate fundus image (4-*f* configuration). The ophthalmic lens OL could be a single lens, an achromatic lens, or an arrangement of different lenses. All lenses could be refractive, diffractive, reflective or hybrid as known to one skilled in the art. The focal length(s) of the ophthalmic lens OL, scan lens SL and the size and/or form of the pupil splitting mirror SM and scanner LnScn could be different depending on the desired field of view (FOV), and so an arrangement in which multiple components can be switched in and out of the beam path, for example by using a flip in optic, a motorized wheel, or a detachable optical element, depending on the field of view can be envisioned. Since the field of view change results in a different beam size on the pupil, the pupil splitting can also be changed in conjunction with the change to the FOV. For example, a 45° to 60° field of view is a typical, or standard, FOV for fundus cameras. Higher fields of view, e.g., a widefield FOV, of 60°-120°, or more, may also be feasible. A widefield FOV may be desired for a combination of the Broad-Line Fundus Imager (BLFI) with another imaging modalities such as optical coherence tomography (OCT). The upper limit for the field of view may be determined by the accessible working distance in combination with the physiological conditions around the human eye. Because a typical human retina has a FOV of 140° horizontal and 80°-100° vertical, it may be desirable to have an asymmetrical field of view for the highest possible FOV on the system.

The scanning line beam SB passes through the pupil Ppl of the eye E and is directed towards the retinal, or fundus, surface F. The scanner LnScn1 adjusts the location of the light on the retina, or fundus, F such that a range of transverse locations on the eye E are illuminated. Reflected or scattered light (or emitted light in the case of fluorescence imaging) is directed back along as similar path as the illumination to define a collection beam CB on a detection path to camera Cmr.

In the "scan-descan" configuration of the present, exemplary slit scanning ophthalmic system SLO-1, light returning from the eye E is "descanned" by scanner LnScn on its way to pupil splitting mirror SM. That is, scanner LnScn scans the illumination beam from pupil splitting mirror SM to define the scanning illumination beam SB across eye E, but since scanner LnScn also receives returning light from eye E at the same scan position, scanner LnScn has the effect of descanning the returning light (e.g., cancelling the scanning action) to define a non-scanning (e.g., steady or stationary) collection beam from scanner LnScn to pupil splitting mirror SM, which folds the collection beam toward camera Cmr. At the pupil splitting mirror SM, the reflected light (or emitted light in the case of fluorescence imaging) is separated from the illumination light onto the detection path directed towards camera Cmr, which may be a digital camera having a photo sensor to capture an image. An imaging (e.g., objective) lens ImgL may be positioned in the detection path to image the fundus to the camera Cmr. As is the case for objective lens ObjL, imaging lens ImgL may be any type of lens known in the art (e.g., refractive, diffractive, reflective or hybrid lens). Additional operational details, in particular, ways to reduce artifacts in images, are described in PCT Publication No. WO2016/124644, the contents of which are herein incorporated in their entirety by reference. The camera Cmr captures the received image, e.g., it creates an image file, which can be further processed by one or more (electronic) processors (CPUs) or computing devices Proc (e.g., the computer system of FIG. 14). This processing unit Proc could be dedicated to data processing or perform other tasks which are quite general and not dedicated to the fundus imager device. The processor (computing device) Proc may include, for example, a field-programmable gate array (FPGA), a digital signal processor (DSP), an application specific integrated circuit (ASIC), a graphics processing unit (GPU), a system on chip (SoC), a central processing unit (CPU), a general purpose graphics processing unit (GPGPU), or a combination thereof, that may performs some, or the entire, processing steps in a serial and/or parallelized fashion with one or more host processors and/or one or more external computing devices. Thus, the collection beam (returning from all scan positions of the scanning line beam SB) is collected by the camera Cmr, and a full-frame image Img may be constructed from a composite of the individually captured collection beams, such as by montaging. However, other scanning configuration are also contemplated, including ones where the illumination beam is scanned across the eye E and the collection beam is scanned across a photo sensor array of the camera. PCT Publication WO 2012/059236 and US Patent Publication No. 2015/0131050, herein incorporated by reference, describe several embodiments of slit scanning ophthalmoscopes including various designs where the returning light is swept across the camera's photo sensor array and where the returning light is not swept across the camera's photo sensor array.

In the present example, the camera Cmr is connected to a processor (e.g., processing module) Proc and a display (e.g., displaying module, computer screen, electronic screen, etc.) Dspl, both of which can be part of the image system itself, or may be part of separate, dedicated processing and/or displaying unit(s), such as a computer system wherein data is passed from the camera Cmr to the computer system over a cable or computer network including wireless networks. The display and processor can be an all in one unit. The display can be a traditional electronic display/screen or of the touch screen type and can include a user interface for displaying information to and receiving information from an instrument operator, or user. The user can interact with the display using any type of user input device as known in the art including, but not limited to, mouse, knobs, buttons, pointer, and touch screen.

It may be desirable for a patient's gaze to remain fixed while imaging is carried out. One way to achieve this is to provide a fixation target that the patient can be directed to stare at. Fixation targets can be internal or external to the instrument depending on what area of the eye is to be imaged. One embodiment of an internal fixation target is shown in FIG. 13. In addition to the primary light source LtSrc used for imaging, a second optional light source FxLtSrc, such as one or more LEDs, can be positioned such that a light pattern is imaged to the retina using lens FxL, scanning element FxScn and reflector/mirror FxM. Fixation scanner FxScn can move the position of the light pattern and reflector FxM directs the light pattern from fixation scanner FxScn to the fundus F of eye E. Preferably, fixation scanner FxScn is position such that it is located at the pupil plane of the system so that the light pattern on the retina/fundus can be moved depending on the desired fixation location.

Slit-scanning ophthalmoscope systems are capable of operating in different imaging modes depending on the light source and wavelength selective filtering elements employed. True color reflectance imaging (imaging similar to that observed by the clinician when examining the eye using a hand-held or slit lamp ophthalmoscope) can be achieved when imaging the eye with a sequence of colored LEDs (red, blue, and green). Images of each color can be built up in steps with each LED turned on at each scanning position or each color image can be taken in its entirety separately. The three, color images can be combined to display the true color image, or they can be displayed individually to highlight different features of the retina. The red channel best highlights the choroid, the green channel highlights the retina, and the blue channel highlights the anterior retinal layers. Additionally, light at specific frequencies (e.g., individual colored LEDs or lasers) can be used to excite different fluorophores in the eye (e.g., autofluorescence) and the resulting fluorescence can be detected by filtering out the excitation wavelength.

The fundus imaging system can also provide an infrared reflectance image, such as by using an infrared laser (or other infrared light source). The infrared (IR) mode is advantageous in that the eye is not sensitive to the IR wavelengths. This may permit a user to continuously take images without disturbing the eye (e.g., in a preview/alignment mode) to aid the user during alignment of the instrument. Also, the IR wavelengths have increased penetration through tissue and may provide improved visualization of choroidal structures. In addition, fluorescein angiography (FA) and indocyanine green (ICG) angiography imaging can be accomplished by collecting images after a fluorescent dye has been injected into the subject's bloodstream. For example, in FA (and/or ICG) a series of time-lapse images may be captured after injecting a light-reactive dye (e.g., fluorescent dye) into a subject's bloodstream. It is noted that care should be taken since the fluorescent dye may lead to a life-threatening allergic reaction in a portion of the population. High contrast, greyscale images are captured using specific light frequencies selected to excite the dye. As the dye flows through the eye, various portions of the eye are made to glow brightly (e.g., fluoresce), making it possible to discern the progress of the dye, and hence the blood flow, through the eye.

Figure 14:
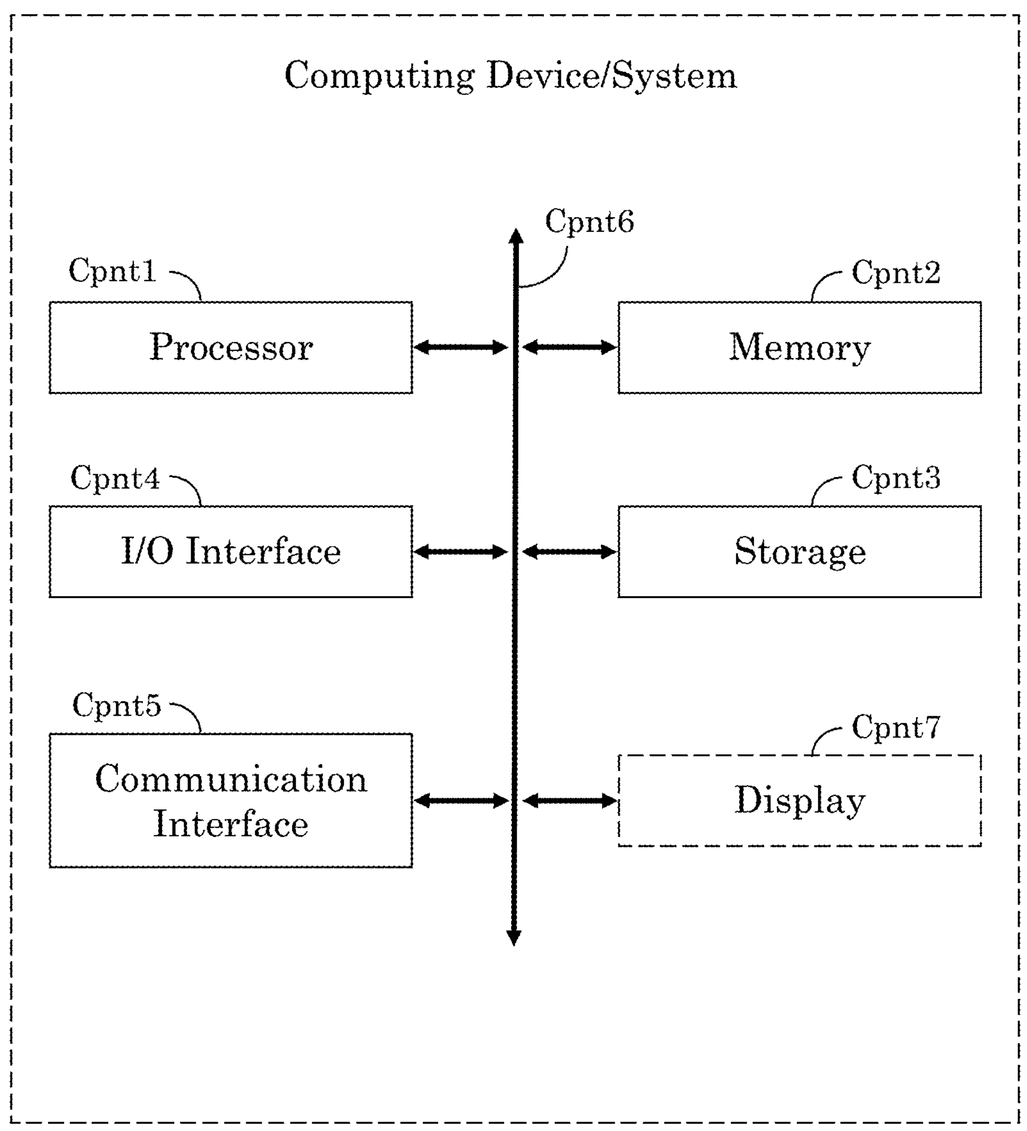
FIG. 14 illustrates an example computer system (or computing device or computer), in accordance with various embodiments.

FIG. 14 illustrates an example computer system (or computing device or computer device). In some embodiments, one or more computer systems may provide the functionality described or illustrated herein and/or perform one or more steps of one or more methods described or illustrated herein. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, an augmented/virtual reality device, or a combination of two or more of these. Where appropriate, the computer system may reside in a cloud, which may include one or more cloud components in one or more networks.

In some embodiments, the computer system may include a processor Cpnt1, memory Cpnt2, storage Cpnt3, an input/output (I/O) interface Cpnt4, a communication interface Cpnt5, and a bus Cpnt6. The computer system may optionally also include a display Cpnt7, such as a computer monitor or screen.

Processor Cpnt1 includes hardware for executing instructions, such as those making up a computer program. For example, processor Cpnt1 may be a central processing unit (CPU) or a general-purpose computing on graphics processing unit (GPGPU). Processor Cpnt1 may retrieve (or fetch) the instructions from an internal register, an internal cache, memory Cpnt2, or storage Cpnt3, decode and execute the instructions, and write one or more results to an internal register, an internal cache, memory Cpnt2, or storage Cpnt3. In various embodiments, processor Cpnt1 may include one or more internal caches for data, instructions, or addresses. Processor Cpnt1 may include one or more instruction caches, one or more data caches, such as to hold data tables. Instructions in the instruction caches may be copies of instructions in memory Cpnt2 or storage Cpnt3, and the instruction caches may speed up retrieval of those instructions by processor Cpnt1. Processor Cpnt1 may include any suitable number of internal registers, and may include one or more arithmetic logic units (ALUs). Processor Cpnt1 may be a multi-core processor; or include one or more processors Cpnt1. Although this disclosure describes and illustrates a particular processor, this disclosure contemplates any suitable processor.

Memory Cpnt2 may include main memory for storing instructions for processor Cpnt1 to execute or to hold interim data during processing. For example, the computer system may load instructions or data (e.g., data tables) from storage Cpnt3 or from another source (such as another computer system) to memory Cpnt2. Processor Cpnt1 may load the instructions and data from memory Cpnt2 to one or more internal register or internal cache. To execute the instructions, processor Cpnt1 may retrieve and decode the instructions from the internal register or internal cache. During or after execution of the instructions, processor Cpnt1 may write one or more results (which may be intermediate or final results) to the internal register, internal cache, memory Cpnt2 or storage Cpnt3. Bus Cpnt6 may include one or more memory buses (which may each include an address bus and a data bus) and may couple processor Cpnt1 to memory Cpnt2 and/or storage Cpnt3. Optionally, one or more memory management unit (MMU) facilitate data transfers between processor Cpnt1 and memory Cpnt2. Memory Cpnt2 (which may be fast, volatile memory) may include random access memory (RAM), such as dynamic RAM (DRAM) or static RAM (SRAM). Storage Cpnt3 may include long-term or mass storage for data or instructions. Storage Cpnt3 may be internal or external to the computer system, and include one or more of a disk drive (e.g., hard-disk drive, HDD, or solid-state drive, SSD), flash memory, ROM, EPROM, optical disc, magneto-optical disc, magnetic tape, Universal Serial Bus (USB)-accessible drive, or other type of non-volatile memory.

I/O interface Cpnt4 may be software, hardware, or a combination of both, and include one or more interfaces (e.g., serial or parallel communication ports) for communication with I/O devices, which may enable communication with a person (e.g., user). For example, I/O devices may include a keyboard, keypad, microphone, monitor, mouse, printer, scanner, speaker, still camera, stylus, tablet, touch screen, trackball, video camera, another suitable I/O device, or a combination of two or more of these.

Communication interface Cpnt5 may provide network interfaces for communication with other systems or networks. Communication interface Cpnt5 may include a Bluetooth interface or other type of packet-based communication. For example, communication interface Cpnt5 may include a network interface controller (NIC) and/or a wireless NIC or a wireless adapter for communicating with a wireless network. Communication interface Cpnt5 may provide communication with a WI-FI network, an ad hoc network, a personal area network (PAN), a wireless PAN (e.g., a Bluetooth WPAN), a local area network (LAN), a wide area network (WAN), a metropolitan area network (MAN), a cellular telephone network (such as, for example, a Global System for Mobile Communications (GSM) network), the Internet, or a combination of two or more of these.

Bus Cpnt6 may provide a communication link between the above-mentioned components of the computing system. For example, bus Cpnt6 may include an Accelerated Graphics Port (AGP) or other graphics bus, an Enhanced Industry Standard Architecture (EISA) bus, a front-side bus (FSB), a HyperTransport (HT) interconnect, an Industry Standard Architecture (ISA) bus, an InfiniBand bus, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or other suitable bus or a combination of two or more of these.

Although this disclosure describes and illustrates a particular computer system having a particular number of particular components in a particular arrangement, this disclosure contemplates any suitable computer system having any suitable number of any suitable components in any suitable arrangement.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

While the systems and methods have been described in conjunction with several specific embodiments, it is evident to those skilled in the art that many further alternatives, modifications, and variations will be apparent in light of the foregoing description. Thus, the systems and methods described herein are intended to embrace all such alternatives, modifications, applications and variations as may fall within the spirit and scope of the appended claims.

The invention claimed is:

1. An eye imaging system for producing images with reduced speckle artifacts, the system comprising:

a single-mode laser diode configured for providing a beam of radiation to the eye;

a photo detector configured for collecting light returning from the eye and generating output signals in response thereto, the photo detector having a sensor integration time; and a driver circuit configured for applying a modulated drive signal to the laser diode, the modulated drive signal configured for inducing a spectral broadening of the beam of radiation during the sensor integration time.

2. The system of claim 1, wherein the single-mode laser diode is designed to operate at a fixed current and wavelength.

3. The system of claim 2, wherein the spectral broadening induced by the modulated drive signal is broader than the spectrum of the laser diode's designed operating wavelength.

4. The system of claim 1, wherein the drive signal is modulated by mode hopping achieved by at least one of shaping a drive current pulse and radio frequency modulation of the laser drive current pulse.

5. The system of claim 1, wherein the drive signal is modulated by imposing a radio frequency (RF) modulation on a drive current pulse.

6. The system of claim 1, wherein the drive signal is modulated by a combination of drive current pulse shaping with high-frequency modulation to generate wavelength diversification to induce speckle reduction.

7. The system of claim 1, wherein the drive signal is modulated by mode hopping achieved by thermal tuning.

8. The system of claim 1, wherein the eye imaging system is a fundus imager.

9. The system of claim 1, wherein the applied modulated drive signal avoids excess drive current.

* * * * *